United States Patent
Di Girolamo et al.

(12) 
(10) Patent No.: US 6,433,238 B1
(45) Date of Patent: Aug. 13, 2002

(54) PROCESS FOR THE PRODUCTION OF HYDROCARBONS WITH A HIGH OCTANE NUMBER BY THE SELECTIVE DIMERIZATION OF ISOBUTENE

(75) Inventors: Marco Di Girolamo, San Donato Milanese; Mario Marchionna, Milan; Lorenzo Tagliabue, Cusano Milanino, all of (IT)

(73) Assignees: Snamprogetti S.p.A., San Donato Milanese; Ecofuel S.p.A., Milan, both of (IT)

( * ) Notice: Subject to any disclaimer, the term of this patent is extended or adjusted under 35 U.S.C. 154(b) by 0 days.

(21) Appl. No.: 09/632,940

(22) Filed: Aug. 4, 2000

(30) Foreign Application Priority Data

Aug. 5, 1999 (IT) .......................................... MI99A1765

(51) Int. Cl.$^7$ ............................. C07C 2/06; C07C 2/26; C07C 2/34
(52) U.S. Cl. ....................................... 585/510; 585/511
(58) Field of Search ................................. 585/510, 511

(56) References Cited

U.S. PATENT DOCUMENTS 4,100,220 A  7/1978  Bowman et al. ....... 260/683.15
5,723,687 A  3/1998  Marchionna et al. ....... 568/647
6,011,191 A  1/2000  Di Girolamo et al.

FOREIGN PATENT DOCUMENTS

EP  0 467 345 A2  1/1992
GB  2 325 237  11/1998

OTHER PUBLICATIONS

U.S. Pat. No. 6,011,191, Di Girolamo et al., filed Jan. 4, 2000.
U.S. application No. 09/632,940, filed Aug. 4, 2000, pending.

*Primary Examiner*—Thuan D. Dang
(74) *Attorney, Agent, or Firm*—Oblon, Spivak, McClelland, Maier & Neustadt, P.C.

(57) ABSTRACT

A process is described for the production of hydrocarbons with a high octane number starting from hydrocarbon cuts containing isobutene by selective dimerization with acid catalysts, characterized in that the dimerization reaction is carried out in the presence of tertiary alcohols, alkyl ethers and primary alcohols in such a quantity as to have, in the feeding, a molar ratio tertiary alcohols+alkyl ethers+primary alcohols/isobutene higher than 0.1, a molar ratio tertiary alcohols/isobutene lower than 0.2 and a molar ratio primary alcohols/isobutene lower than 0.2, preferably operating at a reaction temperature ranging from 30 to 120° C., at a pressure lower than 5 MPa and feeding space velocities of less than 30 h$^{-1}$.

16 Claims, No Drawings

PROCESS FOR THE PRODUCTION OF HYDROCARBONS WITH A HIGH OCTANE NUMBER BY THE SELECTIVE DIMERIZATION OF ISOBUTENE

BACKGROUND OF THE INVENTION

1. Field of the Invention

The present invention relates to a process for the production of hydrocarbons with a high octane number, obtained by the selective dimerization reaction of isobutene contained in hydrocarbon cuts and to a lesser degree of possible linear butenes, in the presence of moderate quantities of tertiary alcohols and alkyl ethers, which favour the production of higher selectivities on the part of the catalyst. The mixture obtained can then be hydrogenated with the conventional methods to obtain a product with further improved octane characteristics.

2. Discussion of the Background

For reasons of an environmental nature, the composition of gasolines is being reformulated to obtain fuels which burn better and have fewer evaporative emissions.

In order to be able to reach this objective, it is necessary to reduce the content of aromatic compounds (mainly benzene), light olefins (photo-chemically reactive and precursors responsible for the formation of atmospheric ozone), sulfur and also the volatility (to minimize losses) and end boiling point of the gasolines.

All these measurements cause a contraction in the volume and a lack in the octane number of the new gasolines, making it necessary, on the basis of the present uncertainty regarding the use of alkyl ethers in fuels (Europ. Chem. News, May 10–16, 1999), to make more and more use of purely hydrocarbon compounds such as, for example, the alkylate.

These products are capable of positively contributing to the above demands as they have a high octane number (both the Research Octane Number (RON) and the Motor Octane Number (MON) are high), excellent boiling point properties (limited volatility but low end point) and they are practically without olefins and aromatics.

At present the alkylate is obtained by the reaction, in liquid phase, between isoparaffinic hydrocarbons, such as for example isobutane, and olefins, for example propylene, butenes, pentenes and relative mixtures, in the presence of an acid catalyst for the production of $C_7$–$C_9$ hydrocarbons with a high octane number to be used in gasolines (see for example: A. Corma, A. Martinez, Catal. Rev.—Sci. Eng., 35, (1993), 483 and references contained therein).

The main problem of the alkylation process is due to the fact that with an increase in regulations of an environmental nature, both traditional processes (with hydrofluoric acid and with sulfuric acid) are coming up against great difficulties, making the future uncertain: the process with hydrofluoric acid owing to the toxicity of this acid, especially in populated areas, and the process with sulfuric acid owing to the large production of acid mud as well as the extremely corrosive power of the catalyst.

Alternative processes with solid acid catalysts are being developed, but their commercial applicability has yet to be demonstrated.

An alternative process in refining for obtaining products with characteristics similar to the alkylate, can be offered by the hydrogenation of the so-called "polymer" gasoline.

The oligomerization process (often erroneously called polymerization in the field of refining) was widely used in the years 1930–1940 to convert low-boiling $C_3$–$C_4$ olefins into gasolines. The process produces a gasoline with a high octane number (RON about 97) but with a high sensitivity owing to the purely olefinic nature of the product (for more specific details on the process see: J. H. Gary, G. E. Handwerk, "Petroleum Refining: Technology and Economics", $3^{rd}$ Ed., M. Dekker, New York, (1994), 250).

Typical olefins which are oligomerized are mainly propylene, which gives slightly higher diners or oligomers depending on the process used, and isobutene which mainly gives dimers but always accompanied by considerable quantities of higher oligomers.

If we limit our attention to the oligomerization of isobutene, it is known that this reaction can be carried out either in batch, semi-continuous or in continuous, in both gas-solid phase and in liquid phase, generally at temperatures ranging from 50 to 300° C. and at atmospheric pressure or at such pressures as to keep the reagents in liquid phase, if considered necessary.

Typical catalysts for the industrial oligomerization process of isobutene are phosphoric acid, generally supported on a solid (for example kieselguhr), or cationic exchange acid resins. The latter enable the use of blander temperature and pressure conditions, with respect to supported phosphoric acid (100° C. and 1–2 Mpa vs 200–220° C. and 3–10 Mpa).

Other catalysts have also been claimed in literature, both liquid acids such as $H_2SO_4$ or sulfonic acid derivatives, or solid acids such as, for example, silico-aluminas, mixed oxides, zeolites, fluorinated or chlorinated aluminas, etc.; none of these catalysts however have as yet allowed the set up of an industrial process such as that of supported phosphoric acid (F. Asinger, "Mono-olefins: Chemistry and Technology", Pergamon Press, Oxford, pages 435–456) and that of cationic resins (G. Scharfe, Hydrocarbon Proc., April 1973, 171).

From the product point of view, the main problem of this process lies in the fact that, in the oligomerization phase, heavy oligomers of isobutene such as trimers (selectivity of 15–30%) and tetramers (selectivity of 1–2%), are produced in excessive percentages. Tetramers are not at all within the gasoline fraction as they are too high-boiling and consequently represent a net loss in yield to gasoline; as far as trimers are concerned (or their hydrogenated derivatives), their concentration should be greatly reduced as their boiling point (170–180° C.) is at the limit of future specifications on the end point of reformulated gasolines.

The problem, on the other hand, of minimizing the formation of higher oligomers to dimers with percentages lower than 10–15% is a typical problem of the oligomerization of isobutene as is also specified in literature (C. T. O'Connor, M. Kojima, K. W. Schumann, Appl. Catal., 16, (1985), 193).

This level of heavy compounds is analogous to that of an alkylate and is still tolerable in the gasoline pool.

From what is described above, it is evident that there is great interest in obtaining a new dimerization process of isobutene which allows the synthesis of a higher quality product, by reaching greater selectivities.

This result can be obtained by carrying out the dimerization reaction of isobutene in the presence of primary alcohols (U.S. Pat. No. 5,723,687 of M. Marchionna, F. Ancilotti and M. Di Girolamo) or mixtures of alkyl ethers and primary alcohols (Italian patent application MI97A001129 of M. Di Girolamo and L. Tagliabue) which, if suitably dosed, make it possible to operate with a catalytic species have the correct activity.

Water can also be used (U.S. Pat. No. 4,100,220 of W. G. Bowton and W. P. Stadig) for regulating the activity of the catalyst, but in this case, in addition to dimerization, there is also the hydration of isobutene with the formation of terbutyl alcohol (TBA) and the consequent decrease in the yield to oligomers.

SUMMARY OF THE INVENTION

It has now been surprisingly found that it is possible to selectively obtain the production of a hydrocarbon fraction, particularly rich in dimers (>85%) and practically without tetramers and higher oligomers (<0.5%), by carrying out the selective dimerization of isobutene in the presence of suitable quantities of tertiary alcohols, alkyl ethers and primary alcohols.

DETAILED DESCRIPTION OF THE INVENTION

The reaction product can then be preferably hydrogenated to give a completely saturated end product with a high octane number and low sensitivity. The hydrogenation can be carried out with conventional methods as described for example in F. Asinger, "Mono-olefins: Chemistry and Technology", Pergamon Press, Oxford, page 455.

As an example, Table I indicates the octane number and relative boiling points of some of the products obtained, using the process of the present invention.

TABLE I

| Product | RON | MON | B.T.(° C.) |
| --- | --- | --- | --- |
| disobutenes | 100 | 89 | 100–105 |
| iso-octane | 100 | 100 | 99 |
| tri-isobutenes | 100 | 89 | 175–185 |
| hydrogenated tri-isobutenes | 101 | 102 | 170–180 |

The process of the present invention for the production of hydrocarbons with a high octane number starting from hydrocarbon cuts containing isobutene by selective dimerization with acid catalysts, is characterized in that the reaction is carried out in the presence of tertiary alcohols, alkyl ethers and primary alcohols in such quantities as to have, in the feeding, a molar ratio tertiary alcohols+alkyl ethers+primary alcohols/isobutene higher than 0.1, preferably ranging from 0.1 to 0.7, a molar ratio tertiary alcohol/isobutene of less than 0.2, preferably ranging from 0.005 to 0.1 and a ratio primary alcohol/isobutene of less than 0.1, preferably ranging from 0.001 to 0.05.

The contemporaneous presence in the reactor of an ether and a tertiary alcohol is fundamental for obtaining the desired high selectivities, these two compounds in fact interact synergistically with the catalyst and allow the formation of a catalytic species with the correct activity, consequently obtaining much better results (in terms of selectivity which is a vital factor in this process) with respect to those obtained when these compounds are used singly in the same quantities.

The fact of operating with the correct catalyst activity makes the reaction much more controllable also from a thermal point of view, with a consequent improvement in the quality of the product.

The alkyl ether, present in a greater quantity, keeps the acid catalyst (which preferably consists of a cationic resin) swollen thus allowing a more effective removal of any possible heavy oligomeric products (formed during the reaction) and consequently a longer average life of the catalyst.

The tertiary alcohol which, owing to its sterical hindrance does not react with the isobutene, is, on the other hand, thanks to its hydroxyl group, capable of interacting much more effectively, with respect to the ether, with the acid centres; a small quantity of alcohol is therefore sufficient for a better regulation of the catalyst activity.

The use of the ether-tertiary alcohol mixture allows, with the same results, the quantity of alkyl ether to be reduced in the reactor (with respect to Italian patent application MI97A001129 of M. Di Girolamo and L. Tagliabue) with a consequent reduction in the running costs of the plant itself.

The presence of ether however is indispensable as the dimerization reaction of isobutene is difficult to handle using tertiary alcohol alone; this alcohol, owing to its high interaction capacity with the catalyst, must be used in small quantities, but under these conditions, it is not able to effectively and uniformly condition the whole of the catalyst causing heterogeneity in the catalytic bed, resulting in the production of mixtures with very low selectivity values.

The primary alcohol present is, on the other hand, necessary for compensating the formation of alkyl ether of diisobutenes.

The correct ratio oxygenated product/hydrocarbon to be used varies in relation to the $C_4$ charge used.

It should also be pointed out that in the case of $C_4$ hydrocarbon streams also comprising linear olefins, it has been observed that at least a part of the latter can be converted by reaction with isobutene into hydrocarbon product without jeopardizing the octane value.

The process claimed herein can be applied to cuts containing isobutene and mixtures with a varying content of isobutane, n-butane and n-butenes.

Although there is a wide range of sources for providing these streams, the most common are those deriving from dehydrogenation processes of iso-paraffins, FCC units, streams coming from steam crackers and the dehydration of terbutanol (coming from the synthesis of propylene oxide) or isobutanol coming from the conversion of $CO/H_2$ mixtures in methanol and higher alcohols (mainly isobutanol).

When steam-cracking streams contain diolefins in addition to the desired mono-olefins, it is necessary to eliminate them with the typical removal treatment (for example extractions or selective hydrogenations).

As well as hydrocarbon components, the stream comprises, as mentioned above, the primary alcohol (in great molar defect with respect to the iso-olefin) and alkyl ether.

The tertiary alcohol used can be selected from tertiary alcohols containing from 4 to 8 carbon atoms: terbutanol (TBA), teramyl alcohol (TAA) and 2,4,4-trimethyl-2-pentanol are preferred.

The alkyl ether used can be selected from those containing from 5 to 10 carbon atoms: MTBE (methyl-ter-butyl ether), ETBE (ethyl-ter-butyl ether), MSBE (methyl-sec-butyl ether), ESBE (ethyl-sec-butyl ether) or mixtures of these are preferred.

The primary alcohol used can be selected from primary alcohols containing from 1 to 7 carbon atoms; methanol and/or ethanol are preferred.

The isobutene, together with the hydrocarbon stream in which it is contained, is sent with the tertiary alcohol, the primary alcohol and alkyl ether, in great stoichiometric defect, into contact with the acid catalyst where the dimerization takes place. The quantity of alkyl ether sent to the reactors is such that, depending on the operating conditions, either its additional production or partial decomposition may take place: in the latter case, as the decomposition process of the ether is endothermic, a part of the heat developed in the dimerization reaction can be absorbed, thus further improving the temperature control in the reactor. In addition, the alcohol released from the decomposition of the ether, as well as interacting with the catalyst, may also react with the dimers and butenes present in the reactor.

The optimum level of the sum of tertiary and primary alcohols and alkyl ether, which must be present in the reaction environment to obtain selectivities to dimers close to or higher than 90% by weight, depends on the composition of the hydrocarbon charge and tendency of the alcohol to react with the $C_4$ and $C_8$ derivatives.

When terbutanol is used as tertiary alcohol, its content must be modulated bearing in mind what can be formed "in situ" due to possible traces of water which may be present in the charge or which can be formed, even if in small quantities, by the condensation reactions of primary alcohols.

When the charge consists of $C_4$ hydrocarbon cuts containing isobutene in weight quantities ranging from 10 to 35% and n-butenes in weight quantities ranging from 25 to 50%, to obtain the best results, it is advisable to operate with a molar ratio tertiary alcohol+alkyl ether+primary alcohol/isobutene ranging from 0.2 to 0.6.

When the charge consists of $C_4$ hydrocarbon cuts containing isobutene in weight quantities ranging from 20 to 60%, n-butenes in weight quantities of more than 30% and $C_4$ paraffins in weight quantities of less than 15%, to obtain the best results, it is advisable to operate with a molar ratio tertiary alcohol+alkyl ether+primary alcohol/isobutene ranging from 0.1 to 0.6.

When the charge consists of $C_4$ hydrocarbon cuts containing isobutene in weight quantities ranging from 30 to 60%, $C_4$ paraffins in weight quantities of more than 30% and n-butenes in weight quantities of less than 10%, to obtain the best results, it is advisable to operate with a molar ratio tertiary alcohol+alkyl ether+primary alcohol/isobutene ranging from 0.3 to 0.7.

When the charge consists of $C_4$ hydrocarbon cuts containing isobutene in weight quantities of more than 80%, to obtain the best results, it is advisable to operate with a molar ratio tertiary alcohol+alkyl ether+primary alcohol/isobutene ranging from 0.4 to 1.

Table II indicates the average compositions of typical $C_4$ hydrocarbon fractions coming from various sources (FCC, Steam Cracking, dehydrogenation of isobutane, streams of isobutene from the dehydration of terbutanol and/or isobutanol).

TABLE II

Percentage compositions typical of $C_4$ streams

|  | Steam Cracking | FCC | Dehydrogenation | Dehydration |
|---|---|---|---|---|
| Isobutene | 30–50 | 10–25 | 45–55 | >90 |
| n-butenes | 35–60 | 25–50 |  | <10 |
| saturated $C_4$ products | 4–8 | 30–60 | 45–55 | <10 |

For charges different from those generally available in industrial practice, it can be seen that the addition of significant quantities of linear olefins with respect to the charge compositions mentioned above, causes a slight increase in the selectivity to dimers and consequently a slight reduction in the lower limit of the molar ratio primary alcohol+tertiary alcohol+alkyl ether/isobutene previously indicated. An increase in the saturated hydrocarbon content, on the contrary, causes a slight decrease in the selectivity which means that the lower limit value of the ratio is slightly increased.

A wide variety of acid catalysts can be used for this process, of which mineral acids such as sulfuric acid, $BF_3$, supported phosphoric acid, zeolites suitably modified, heteropolyacids and sulfonated polymer resins, for example Amberlyst 15 and Amberlyst 35, can be mentioned as examples. Among these catalysts the use of sulfonated, macro-lattice resins, generally copolymers of styrene and benzene, is preferred; the characteristics of these resins are widely described in literature (see for example A. Mitschker, R. Wagner, P. M. Lange, "Heterogeneous Catalysis and Fine Chemicals", M. Guisnet ed., Elsevier, Amsterdam, (1988), 61).

A vast range of operating conditions can be used for the production of hydrocarbons with a high octane number from isobutene in the desired selectivities by means of the object of the present invention. It is possible to operate in vapor phase or liquid-vapor phase but the operating conditions in liquid phase are preferred.

The process of the present invention can operate under both batch and continuous conditions, bearing in mind, however, that the latter are much more advantageous in industrial practice. The preferred reactor configuration can be optionally selected from fixed-bed, tubular fixed-bed, adiabatic, stirred and finally column reactor which also allows separation of the products (a description of the general use of this technology is provided for example in: J. L. De Garmo, V, N. Parulekar, V. Pinjala, Chem. Eng. Progr., March 1992, 43).

The field of process conditions, operating in liquid phase, comprises a wide variety of operating conditions which are described hereunder.

The pressure is preferably superatmospheric to keep the reagents in liquid phase, generally below 5 Mpa, more preferably between 0.2 and 2.5 Mpa. The reaction temperature preferably ranges from 30 to 120° C.

The feeding space velocities of the alcohol-hydrocarbon stream are preferably less than 30 $h^{-1}$, more preferably between 1 and 15 $h^{-1}$.

The isobutene is mainly converted in the reaction zone, part of the n-olefins however can also be converted to useful product; there are basically no limits for the concentration of iso-olefin in the hydrocarbon fraction even if it is preferable to have concentrations ranging from 2 to 60%; there are no limits in the ratio between isobutene and linear olefins. It should be noted that in the case of streams coming from the dehydrogenation of isobutane, the concentrations of linear butenes in the charge are not significant.

Some examples are provided for a better illustration of the invention but in no way limit its scope.

EXAMPLE 1

This example illustrates the use of the process of the present invention in a jacketed tubular reactor in which the reaction heat is removed by circulation of a cooling fluid in the reactor jacket (average ΔT of about 20° C.).

The catalyst used is a commercial sulfonated macroporous resin of the Amberlyst 35 type produced by Rohm & Haas, Co. A constant pressure of 1.5 Mpa, sufficient to keep the reagents liquid, was maintained in the reactor.

In this test a hydrocarbon stream having the following composition was used:

| | | |
|---|---|---|
| isobutene | : | 20% by weight |
| n-butenes | : | 70% by weight |
| saturated C$_4$ products: | : | 10% by weight |

The reaction was carried out at an LHSV space velocity of 10 volumes of feeding/hour per volume of catalyst (10 h$^{-1}$) using as oxygenated compounds methanol (MeOH), terbutanol (TBA) and methylterbutylether (MTBE) in the following molar ratios:

| | | |
|---|---|---|
| MeOH + MTBE + TBA/isobutene | : | 0.22 |
| TBA/isobutene | : | 0.02 |
| MeOH/IB | : | 0.005 |

Under these conditions, a conversion of isobutene of 75% was obtained (once the stationary state had been reached), with a selectivity to C$_8$ of 90% by weight.

The product obtained therefore had the following composition:

| | | |
|---|---|---|
| C$_8$ HYDROCARBON | : | 90.1% w |
| C$_{12}$ HYDROCARBON | : | 9.5% w |
| C$_{16}$ HYDROCARBON | : | 0.4% w |

EXAMPLE 2
(Comparative)

This example shows how, by maintaining the MTBE constant with respect to example 1, in the absence of TBA, it is not possible to limit the formation of heavy oligomers.

This example was carried out using the same operating conditions and the same equipment described in example 1.

Under these conditions, a conversion of isobutene of 87% was obtained (once the stationary state had been reached), with a low selectivity to C$_8$ of 82% by weight.

The product obtained therefore had the following composition:

| | | |
|---|---|---|
| C$_8$ HYDROCARBON | : | 81.9% w |
| C$_{12}$ HYDROCARBON | : | 17.0% w |
| C$_{16}$ HYDROCARBON | : | 1.1% w |

EXAMPLE 3
(Comparative)

This example shows how, with respect to example 2, to obtain a hydrocarbon product of the desired quality without terbutyl alcohol, the quantity of MTBE must be tripled.

This example was carried out using the same operating conditions and the same equipment as example 2 and a molar ratio MTBE/isobutene of 0.6.

Under these conditions, a conversion of isobutene of 76% was obtained (once the stationary state had been reached), with a selectivity to C$_8$ of 90.7% by weight.

The product obtained therefore had the following composition:

| | | |
|---|---|---|
| C$_8$ HYDROCARBON | : | 90.7% w |
| C$_{12}$ HYDROCARBON | : | 8.9% w |
| C$_{16}$ HYDROCARBON | : | 0.4% w |

EXAMPLE 4
(Comparative)

This example shows, on the other hand, how the use of ether is indispensable for a better conditioning of the catalyst. On carrying out the test with TBA alone (molar ratio 0.04), it was not possible to control the dimerization of isobutene with irregular temperature shifts in the reactor which even reached 120° C. (ΔT of over 60° C.). This example was carried out using the same operating conditions and the same equipment described in example 1.

Under these conditions, a conversion of isobutene of 94% was obtained (once the stationary state had been reached), with a low selectivity to C$_8$ of 78% by weight.

The product obtained therefore had the following composition:

| | | |
|---|---|---|
| C$_8$ HYDROCARBON | : | 77.9% w |
| C$_{12}$ HYDROCARBON | : | 20.3% w |
| C$_{16}$ HYDROCARBON | : | 1.8% w |

What is claimed is:

1. A process for the production of hydrocarbons with a high octane number comprising:

selectively dimerizing a feed comprising hydrocarbon cuts comprising isobutene with acid catalysts, wherein the dimerization reaction is carried out in the presence of primary alcohols, tertiary alcohols and alkyl ethers in such a quantity as to have a molar ratio in the feed of tertiary alcohol+alkyl ether+primary alcohol/isobutene higher than 0.1, a molar ratio of tertiary alcohol/isobutene lower than 0.2 and a molar ratio of primary alcohol/isobutene lower than 0.1.

2. The process according to claim 1, operating at a reaction temperature ranging from 30 to 120° C., at a pressure of less than 5 Mpa and feed space velocities of less than 30 h$^{-1}$.

3. The process according to claim 1, wherein the molar ratio in the feed of

Tertiary alcohols+alkyl ethers+primary alcohols/isobutene ranges from 0.1 to 1.

4. The process according to claim 1, wherein the molar ratio in the feed of tertiary alcohols/isobutene ranges from 0.05 to 0.1.

5. The process according to claim 1, wherein the molar ratio in the feed of primary alcohols/isobutene ranges from 0.001 to 0.05.

6. The process according to claim 1, wherein the feed comprises hydrocarbon cuts containing isobutene in a quantity ranging from 10 to 35% by weight and n-butenes in a quantity ranging from 25 to 50% by weight and the molar ratio of tertiary alcohols+alkyl ethers+primary alcohols/isobutene ranges from 0.2 to 0.6.

7. The process according to claim 1, wherein the feed comprises hydrocarbon cuts containing isobutene in a quantity ranging from 20 to 60% by weight and n-butenes in a quantity of more than 30% by weight and $C_4$ paraffins in a quantity of less than 15% by weight and the molar ratio of $$\text{tertiary alcohols+alkyl ethers+primary alcohols/isobutene ranges from 0.1 to 0.6.}$$

8. The process according to claim 1, wherein the feed comprises hydrocarbon cuts containing isobutene in a quantity ranging from 30 to 60%, $C_4$ paraffins in quantities of over 30% by weight and n-butenes in quantities of less than 10% by weight and the molar ratio of $$\text{tertiary alcohols+alkyl ethers+primary alcohols/isobutene ranges from 0.3 to 0.7.}$$

9. The process according to claim 1, wherein the feed comprises hydrocarbon cuts containing isobutene in quantities of over 80% by weight and the molar ratio of tertiary alcohols+alkyl ethers+primary alcohols/isobutene ranges from 0.4 to 18.

10. The process according to claim 1, wherein the space velocities in the feed range from 1 to 15 $h^{-1}$.

11. The process according to claim 1, wherein the primary alcohol has from 1 to 6 carbon atoms.

12. The process according to claim 11, wherein the primary alcohol is selected from the group consisting of methanol, ethanol and mixtures thereof.

13. The process according to claim 1, wherein the alkyl ether has from 5 to 10 carbon atoms.

14. The process according to claim 13, wherein the alkyl ether is selected from the group consisting of MTBE, ETBE, MSBE, ESBE and mixtures thereof.

15. The process according to claim 1, wherein the tertiary alcohol has from 4 to 8 carbon atoms.

16. The process according to claim 15, wherein the tertiary alcohol is selected from the group consisting of terbutyl alcohol, teramyl alcohol, 2,4,4-trimethyl-2-pentanol and mixtures thereof.

* * * * *